US011221484B2

(12) United States Patent
Choi et al.

(10) Patent No.: US 11,221,484 B2
(45) Date of Patent: Jan. 11, 2022

(54) APPARATUS AND METHOD FOR SCENT VISUALIZATION

(71) Applicant: Electronics and Telecommunications Research Institute, Daejeon (KR)

(72) Inventors: Jong Woo Choi, Daejeon (KR); Jun Seok Park, Daejeon (KR); Joon Hak Bang, Daejeon (KR); Hae Ryong Lee, Daejeon (KR); Sung June Chang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 213 days.

(21) Appl. No.: 16/601,330

(22) Filed: Oct. 14, 2019

(65) Prior Publication Data

US 2020/0132999 A1 Apr. 30, 2020

(30) Foreign Application Priority Data

Oct. 24, 2018 (KR) .................. 10-2018-0127778

(51) Int. Cl.
*G02B 27/01* (2006.01)
*G06N 3/08* (2006.01)
*G06K 9/62* (2006.01)
*A61L 9/12* (2006.01)

(52) U.S. Cl.
CPC .......... *G02B 27/0172* (2013.01); *A61L 9/125* (2013.01); *G06K 9/6256* (2013.01); *G06N 3/08* (2013.01); *G02B 2027/014* (2013.01); *G02B 2027/0138* (2013.01)

(58) Field of Classification Search
CPC combination set(s) only.
See application file for complete search history.

(56) References Cited

U.S. PATENT DOCUMENTS

| 2009/0106820 | A1  | 4/2009  | Park et al. |
|---|---|---|---|
| 2012/0308121 | A1* | 12/2012 | Datta ................... G06K 9/6263 382/155 |
| 2013/0120788 | A1* | 5/2013  | Wang ...................... G06K 9/00 358/1.15 |
| 2015/0039421 | A1* | 2/2015  | Ford .................. G06Q 30/0252 705/14.49 |
| 2016/0359740 | A1* | 12/2016 | Parandehgheibi .... G06F 16/248 |

(Continued)

FOREIGN PATENT DOCUMENTS

| JP | 2018109099 A | 7/2018 |
|---|---|---|
| KR | 100665353 B1 | 1/2007 |

(Continued)

*Primary Examiner* — Zhiyu Lu
(74) *Attorney, Agent, or Firm* — William Park & Associates Ltd.

(57) ABSTRACT

A scent visualization system may comprise a display apparatus for generating a target image including a target object; an olfactory sensor for detecting a scent; and a scent visualization apparatus for generating target associative visualization information that reminds the scent from the target image received from the display apparatus and sensing information received from the olfactory sensor, and generating an associative image by combining the target associative visualization information and the target image. Therefore, a low-cost, high-efficiency, high-utilization, and high-convenience scent visualization system can be provided.

19 Claims, 5 Drawing Sheets

(56) References Cited

U.S. PATENT DOCUMENTS

| | | | |
|---|---|---|---|
| 2017/0343521 A1 | 11/2017 | Chang et al. | |
| 2018/0293050 A1* | 10/2018 | Bolden | G06F 40/40 |
| 2018/0369847 A1* | 12/2018 | Kihm | B05B 13/005 |
| 2019/0019033 A1* | 1/2019 | Chang | G06F 16/48 |
| 2019/0025773 A1* | 1/2019 | Yang | G06K 9/036 |
| 2019/0087425 A1* | 3/2019 | Kim | G06N 3/04 |
| 2019/0221121 A1* | 7/2019 | Guo | G08G 1/20 |
| 2020/0193299 A1* | 6/2020 | Geva | G06K 9/6272 |
| 2020/0341540 A1* | 10/2020 | Jin | G06F 3/016 |

FOREIGN PATENT DOCUMENTS

| | | |
|---|---|---|
| KR | 101133059 B1 | 4/2012 |
| KR | 1020160071000 A | 6/2016 |

* cited by examiner

APPARATUS AND METHOD FOR SCENT VISUALIZATION

CROSS-REFERENCE TO RELATED APPLICATIONS

This application claims priority to Korean Patent Application No. 10-2018-0127778 filed on Oct. 24, 2018 in the Korean Intellectual Property Office (KIPO), the entire contents of which are hereby incorporated by reference.

BACKGROUND

1. Technical Field

The present disclosure relates to a method and an apparatus for scent visualization, and more specifically, to a method and an apparatus for providing an image reminiscent of olfactory information.

2. Related Art

With the development of computers and information and communication technologies, interest in multi-sensory content technology is increasing. The multi-sensory content technology is a technology that expresses people's five senses through various information and communication technology ICT) devices. Recently, attention has been paid to a technique of enhancing immersion feeling of contents and expressing the senses in various forms.

Technologies for providing visual information and auditory information, which are considered to be main senses among the five senses of human, have been universally provided using camera, microphone, screen, speaker, and the like with the development of display technologies, music, and sound effect technologies. On the other hand, technologies for providing olfactory information, tactile information, and taste information have technical problems in recognition and reproduction of sensory data, and have difficulty in operation. For example, a conventional scent providing apparatus for providing olfactory information includes sensors and scent cartridges, thereby recognizing a surrounding scent by the sensors, analyzing it and converting it into a digital olfactory signal, and reproducing a scent that is matched to a type and a concentration of the analyzed scent.

However, the conventional scent providing apparatus has a disadvantage that the types of scents that can be expressed by the scent cartridges are limited, it is difficult to accurately express the recognized scent, and the scent is diluted or hardened thereby making it difficult to smell. In addition, since the states of the scent cartridges should be periodically checked in order to prevent the contents in the scent cartridges from being exhausted, regular maintenance is indispensable.

SUMMARY

Accordingly, embodiments of the present disclosure provide a low-cost, high-efficiency, high-utilization, and high-convenience scent visualization system.

Also, embodiments of the present disclosure provide a low-cost, high-efficiency, high-utilization, and high-convenience scent visualization apparatus.

Also, embodiments of the present disclosure provide a low-cost, high-efficiency, high-utilization, and high-convenience scent visualization method.

In order to achieve the objective of the present disclosure, a scent visualization method of a scent visualization apparatus interworking with a display apparatus and an olfactory sensor may comprise receiving a target image including a target object from the display apparatus; receiving sensing information from the olfactory sensor; outputting first associative visualization information on the target image using a first learning model; outputting second associative visualization information on the sensing information using a second learning model; comparing the first associative visualization information and the second associative visualization information to select target associative visualization information having a higher similarity; and combining the selected target associative visualization information and the target image to generate an associative image.

The first learning model may be generated through machine learning by extracting visualization information representing first basic data which is olfactory sensibility information of the target object with visual attribute information, and extracting the first associative visualization information having a high similarity among the visualization information.

The second learning model may be generated through machine learning by extracting visualization information representing second basic data which is olfactory sensitivity information of the sensing information with visual attribute information, and extracting the second associative visualization information having a high similarity among the visualization information.

The visualization information may be represented by at least one of an attribute representing a particle effect, an icon, an illustration, a photograph, and a constellation.

The first associative visualization information and the second associative visualization information may be extracted using a softmax algorithm.

The display apparatus may be a head mounted display (HMD) apparatus.

The scent visualization method may further comprise generating a least one scent corresponding to the sensing information by interworking with a scent diffusion apparatus.

In order to achieve the objective of the present disclosure, a scent visualization apparatus may comprise a processor and a memory storing at least one instruction executable by the processor. Also, when executed by the processor, the at least one instruction may be configured to interwork with a display apparatus and an olfactory sensor; receive a target image including a target object from the display apparatus; receive sensing information from the olfactory sensor; output first associative visualization information on the target image using a first learning model; output second associative visualization information on the sensing information using a second learning model; compare the first associative visualization information and the second associative visualization information to select target associative visualization information having a higher similarity; and combine the selected target associative visualization information and the target image to generate an associative image.

The scent visualization apparatus may further comprise a communication unit providing a communication network for interworking with the display apparatus and the olfactory sensor.

The scent visualization apparatus may further comprise a storage unit for storing data, wherein the storage unit comprises a first storage unit storing first basis data which is olfactory sensibility information of the target image; a second storage unit storing second basic data which is olfactory sensibility information of the sensing information; and a third storage unit storing the first learning model and the second learning model.

The at least one instruction may be further configured to learn the first basic data; learn the second basic data; generate the first learning model; and generate the second learning model.

The first learning model may be generated through machine learning by extracting visualization information representing the first basic data with visual attribute information, and extracting the first associative visualization information having a high similarity among the visualization information.

The second learning model may be generated through machine learning by extracting visualization information representing the second basic data with visual attribute information, and extracting the second associative visualization information having a high similarity among the visualization information.

The visualization information may be represented by at least one of an attribute representing a particle effect, an icon, an illustration, a photograph, and a constellation.

The first associative visualization information and the second associative visualization information may be extracted using a softmax algorithm.

The display apparatus may be a head mounted display (HMD) apparatus.

The at least one instruction may be further configured to generate a least one scent corresponding to the sensing information by interworking with a scent diffusion apparatus.

In order to achieve the objective of the present disclosure, a scent visualization system may comprise a display apparatus for generating a target image including a target object; an olfactory sensor for detecting a scent; and a scent visualization apparatus for generating target associative visualization information that reminds the scent from the target image received from the display apparatus and sensing information received from the olfactory sensor, and generating an associative image by combining the target associative visualization information and the target image.

The scent visualization system may further comprise a scent diffusion apparatus generating at least one scent corresponding to the sensing information.

First associative visualization information on the target image may be output using a first learning model, second associative visualization information on the sensing information may be output using a second learning model, and associative visualization information having a higher similarity among the first associative visualization information and the second associative visualization information may be selected as the target associative visualization information.

According to the embodiments of the present disclosure, a high-efficiency scent visualization system and method capable of generating a real-time associative image by pre-generating learning models based on basic data can be provided. Also, a low-cost and high-efficiency scent visualization apparatus capable of generating the associative image only by interworking with a display apparatus without any further additional apparatus can be provided.

Further, since the scent visualization system and apparatus according to the embodiments of the present disclosure do not require any additional maintenance when using the system and apparatus, a high-convenience scent visualization system can be provided. Also, the scent visualization system and method according to the embodiments of the present disclosure can be easily compatible with external devices.

BRIEF DESCRIPTION OF DRAWINGS

Embodiments of the present disclosure will become more apparent by describing in detail embodiments of the present disclosure with reference to the accompanying drawings, in which.

DETAILED DESCRIPTION

Embodiments of the present disclosure are disclosed herein. However, specific structural and functional details disclosed herein are merely representative for purposes of describing embodiments of the present disclosure, however, embodiments of the present disclosure may be embodied in many alternate forms and should not be construed as limited to embodiments of the present disclosure set forth herein.

Accordingly, while the present disclosure is susceptible to various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is to cover all modifications, equivalents, and alternatives falling within the spirit and scope of the present disclosure. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present disclosure will be described in detail with reference to the accompanying drawings. In order to facilitate the understanding of the present disclosure, the same reference numerals are used for the same constituent elements in the drawings and redundant explanations for the same constituent elements are omitted.

Figure 1:
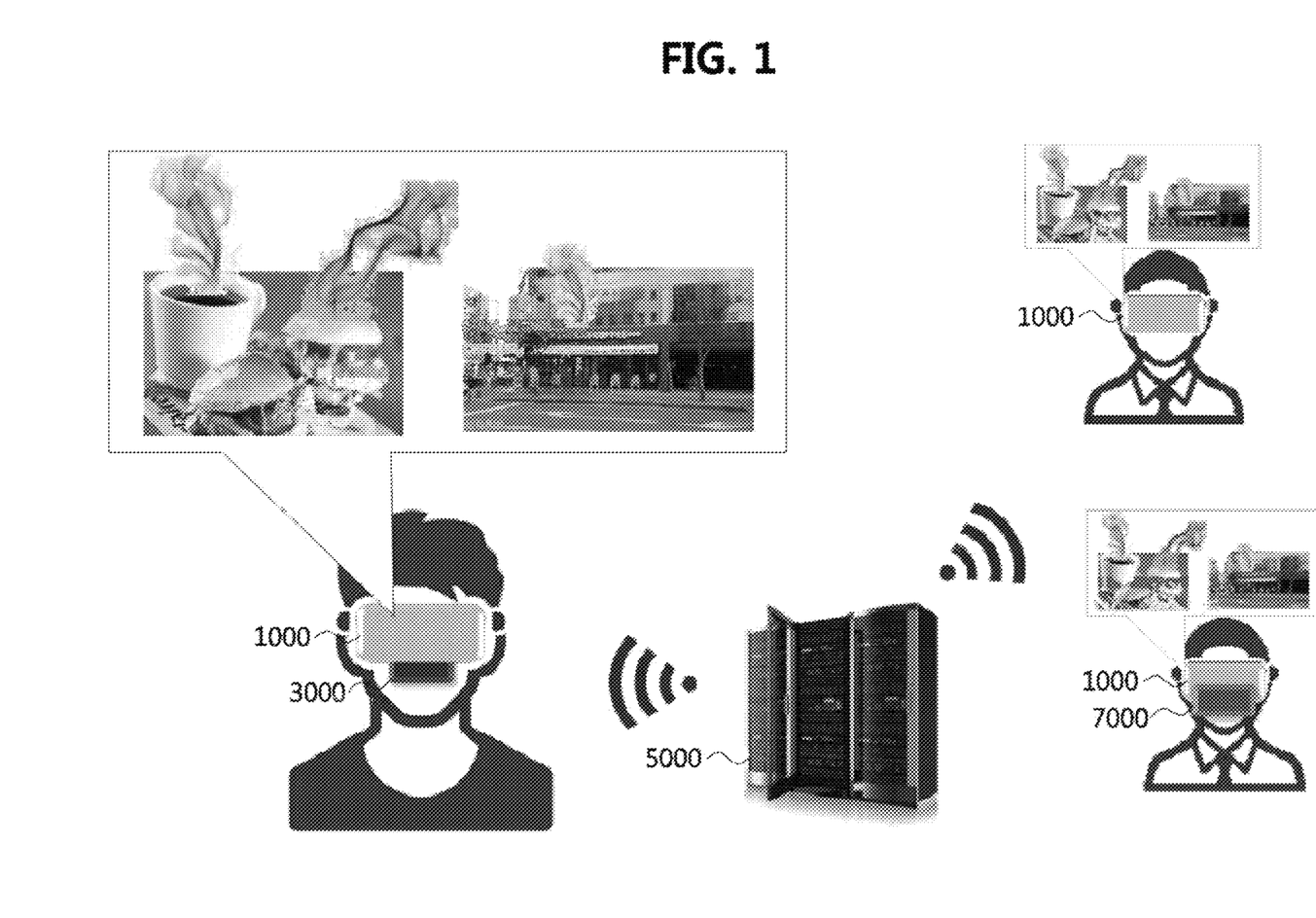
FIG. 1 is a conceptual diagram illustrating a scent visualization system according to an embodiment of the present disclosure.

FIG. 1 is a conceptual diagram illustrating a scent visualization system according to an embodiment of the present disclosure.

Referring to FIG. 1, a scent visualization system may include a display apparatus 1000, an olfactory sensor apparatus 3000, and a scent visualization apparatus 5000.

The scent visualization system may be provided in a structure in which the display apparatus 1000 and the olfactory sensor apparatus 3000 are interworking with the scent visualization apparatus 5000. Accordingly, the scent visualization apparatus may receive at least one target image and at least one sensing information from the display apparatus 1000 and the olfactory sensor apparatus 3000, and may provide a user with an associative image reminiscent of a specific scent for the target image. Here, the target image may be an image of a specific object recognized from a video display unit 1100 in the display apparatus 1000.

In addition, the scent visualization system may interwork with a scent diffusion apparatus 7000. When the scent visualization system interworks with the scent diffusion apparatus, the scent diffusion apparatus 7000 may receive sensing information generated by the scent visualization apparatus 5000, and may generate a scent corresponding to the sensing information. Accordingly, the scent visualization system may provide a more realistic sensory effect by providing the user with an association effect and a scent with respect to the target image.

In the following description, with reference to FIGS. 2 to 4, the display apparatus 1000, the olfactory sensor apparatus 300, and the scent visualization apparatus 5000, which are components of the scent visualization system, will be described in further detail.

Figure 2:
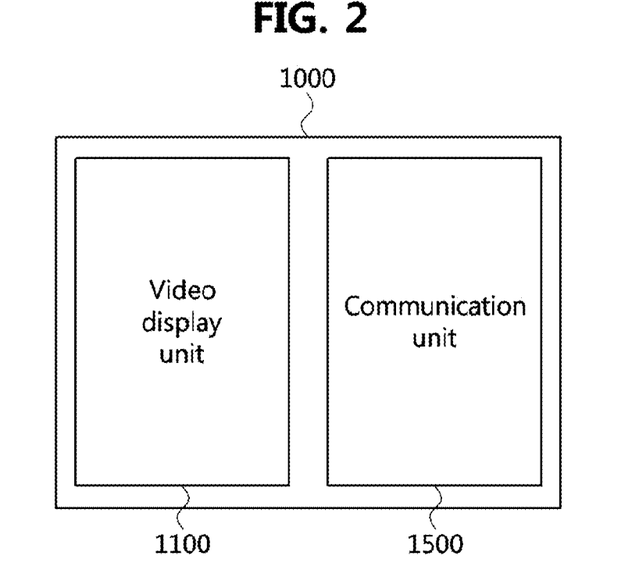
FIG. 2 is a block diagram illustrating a display apparatus according to an embodiment of the present disclosure.

FIG. 2 is a block diagram illustrating a display apparatus according to an embodiment of the present disclosure.

Referring to FIG. 2, the display apparatus 1000 may be mounted on a head of the user to provide visual information to the user. According to an embodiment, the display apparatus 1000 may support an image technology environment such as augmented reality (AR), virtual reality (VR), and mixed reality (MR). For example, the display apparatus 1000 may be provided in a form of a head mounted display (HMD). The display apparatus 1000 may include a video display unit 1100 and a communication unit 1500.

The video display unit 1100 may be provided as a see-through display panel. Accordingly, the user may secure a forward view even when the display apparatus 1000 is mounted. However, the display apparatus 1100 is not limited to the specific embodiment, and various embodiments in which the forward view of the user can be secured even when the display apparatus is mounted may be applied.

The video display unit 1100 may display an associative image received from the scent visualization apparatus 5000 to be described later. Here, the associative image may be an image that combines associative visualization information and a target image, and may be an image that induces the user to remind a specific scent. As described above, the target image may be an image of a specific object recognized in the image displayed on the video display unit 1100. The associative image will be described more specifically in the description of a processor 1500 to be described later.

Also, the video display unit 1100 may display at least one video image. According to an embodiment, the video image may be a front image of the user or a processed video image received from the outside.

The communication unit 1500 may provide a communication network for interworking with the scent visualization apparatus 5000. Accordingly, as described above, the communication unit 1500 may transmit the target image to the scent visualization apparatus 5000 and may receive the associative image from the scent visualization apparatus 5000. According to an embodiment, the communication unit 1500 may provide a wired or wireless communication network. However, the communication unit 1500 is not limited to the specific embodiment, and may provide various communication environments capable of transmitting and receiving data.

Figure 3:
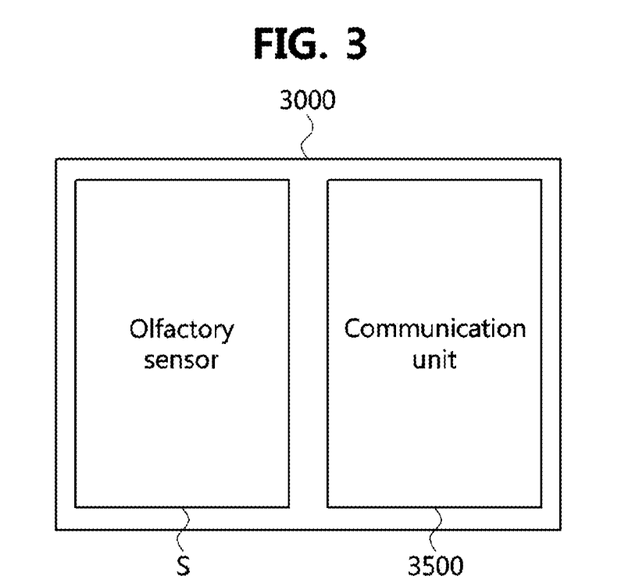
FIG. 3 is a block diagram illustrating an olfactory sensor according to an embodiment of the present disclosure.

FIG. 3 is a block diagram illustrating an olfactory sensor according to an embodiment of the present disclosure.

Referring to FIG. 3, the olfactory sensor apparatus 300 may include at least one olfactory sensor S, and a communication unit 3500.

The olfactory sensor apparatus 3000 may sense scents generated in the vicinity by using the at least one olfactory sensor S. According to an embodiment, the at least one olfactory sensor S may include at least one of a semiconductor gas sensor, an electrochemical gas sensor, and an optical gas sensor. The at least one olfactory sensor S may sense the scents and generate sensing information. According to an embodiment, the sensing information may include at least one of concentration and attribute information of the sensed scents. For example, when a semiconductor gas sensor and an electrochemical gas sensor are used, a concentration change of a specific gas may be expressed by an analog-to-digital converter (ADC) value or a resistance value. Also, when the olfactory sensor apparatus 3000 uses an optical gas sensor, a concentration change of a specific gas may be expressed by a spectrum image.

The communication unit 3500 may provide a communication network for interworking with the scent visualization apparatus 5000, similarly to the communication unit 1500 in the display apparatus 1000 described above. Accordingly, the olfactory sensor apparatus may transmit sensing information to the scent visualization apparatus 5000 by using the communication unit 3500.

Here, the transmitted sensing information may be used as information for generating associative visualization information in the scent visualization apparatus 5000, like the target image described above. The association effect will be described more specifically in the description of the scent visualization apparatus 5000 to be described later.

Figure 4:
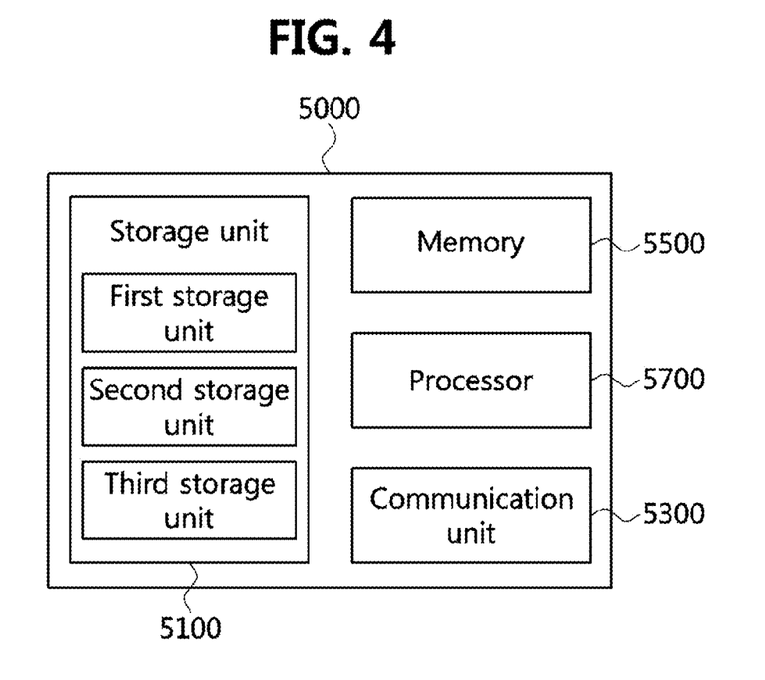
FIG. 4 is a block diagram illustrating a scent visualization apparatus according to an embodiment of the present disclosure.

FIG. 4 is a block diagram illustrating a scent visualization apparatus according to an embodiment of the present disclosure.

Referring to FIG. 4, the scent visualization apparatus 5000 may interwork with the display apparatus 1000 and the olfactory sensor apparatus 3000 to generate the associative visualization information from the at least one target image and the at least one sensing information which are received from the apparatuses 1000 and 3000.

More specifically, the scent visualization apparatus 5000 may include a storage unit 5100, a communication unit 5300, a memory 5500, and a processor 5700.

The storage unit 5100 may store the information received by the communication unit 5300, which will be described later. According to an embodiment, the storage unit 5100 may include a first storage unit 5110 and a second storage unit 5130.

The first storage unit 5110 may store first basic data for generating a first learning model by the processor 5700 to be described later. Here, the first basic data may be at least one olfactory sensibility information felt from at least one specific object. In other words, the first basic data may be table data mapping corresponding olfactory sensibility information to various specific objects. The first storage unit 5110 may collect and store the first basic data from a plurality of users or an external big data server by the communication unit 5300 to be described later. For example, the first storage unit 5110 may classify and store the first basic data according to attribute information of particles.

The second storage unit 5130 may store second basic data for generating a second learning model by the processor 5700 to be described later. Here, the second basic data may be at least one olfactory sensibility information felt from at least one sensing information. Here, the sensing information may be pre-acquired information other than those transmitted from the olfactory sensor apparatus 3000 or sensing information received from the outside. In other words, the second basic data may be table data mapping corresponding olfactory sensibility information to various sensing information. Similarly to the first storage unit 5110, the second storage unit 5130 may collect and store the second basic data from a plurality of users or an external big data server by the communication unit 5300 to be described later. For example, the second storage unit 5130 may classify and store the second basic data according to attribute information of particles.

The third storage unit 5150 may store the first learning model and the second learning model generated by the processor 5700, which will be described later. Here, the first learning model may be a learning model for outputting first association visualization information on the target image received from the display apparatus 1000. Also, the second learning model may be a learning model for outputting second associative visualization information on the sensing information received from the olfactory sensor apparatus 3000. A method of generating the first and second associative visualization information from the first learning model and the second learning model will be described in more detail in the description of the operation of the processor 5700 described below.

The communication unit 5300 may provide a communication network for interworking with at least one of the display apparatus 1000 and the olfactory sensor apparatus 3000. Accordingly, the communication unit 5300 may transmit and receive at least one piece of data and information to and from the components 1000 and 3000.

The memory 5500 may include at least one instruction executable by the processor 5700 described below. At least one instruction may cause the processor 5700 to perform the scent visualization method according to an embodiment of the present disclosure. The processor 5700 may execute the at least one instruction stored in the memory 5500, as described above. The operation of the processor 5700 will be described in more detail in the following description of the scent visualization method.

The scent visualization system according to an embodiment of the present disclosure has been described above. The conventional scent providing apparatus has a disadvantage in that maintenance is difficult and expression of scent is limited by using a scent diffusion apparatus including scent cartridges.

However, since the scent visualization system according to the embodiment of the present disclosure includes the display apparatus, the olfactory sensor apparatus, and the scent visualization apparatus, a separate scent diffusion apparatus difficult to maintain is not necessarily required, and thus it is possible to provide the low-cost, high-efficiency, and high-convenience scent visualization system.

Hereinafter, a scent visualization method will be described based on operations of the processor in the scent visualization apparatus.

Figure 5:
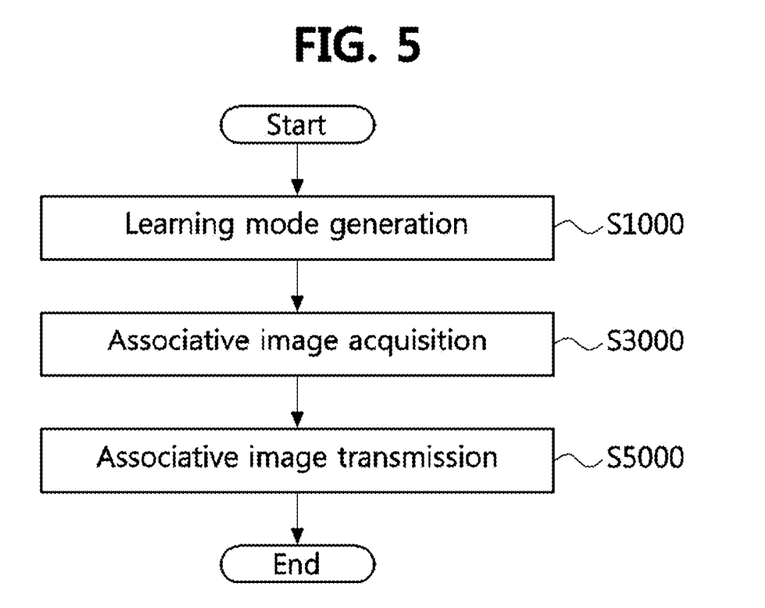
FIG. 5 is a flowchart illustrating a scent visualization method according to an embodiment of the present disclosure.

FIG. 5 is a flowchart illustrating a scent visualization method according to an embodiment of the present disclosure.

Referring to FIG. 5, the processor 5700 in the scent visualization apparatus according to an embodiment of the present invention may generate learning models (S1000). Here, the learning model may be a basic model for generation of associative visualization information on the target image and the sensing information. The step of generating the learning models will be described in more detail with reference to FIG. 6.

Figure 6:
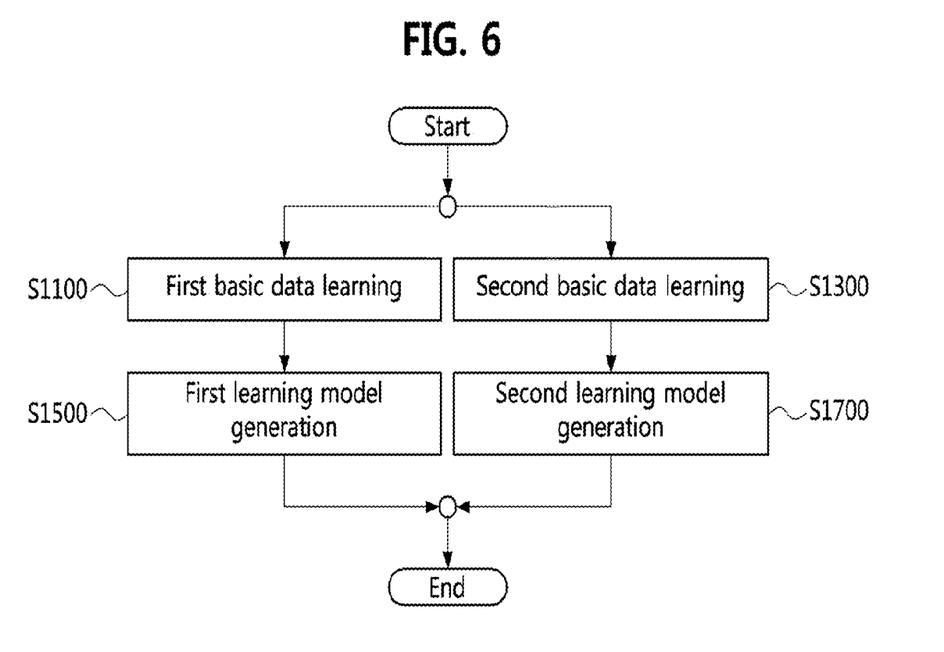
FIG. 6 is a flowchart illustrating a step of generating learning models in a scent visualization method according to an embodiment of the present disclosure.

FIG. 6 is a flowchart illustrating a step of generating learning models in a scent visualization method according to an embodiment of the present disclosure.

Referring to FIG. 6, the processor 5700 may learn first basic data (S1100). In other words, the processor 5700 may extract first associative visualization information associated with a specific target image.

More specifically, the processor 5700 may learn visualization information reminiscent of the first basic data. Here, the visualization information may be information that visually expresses olfactory sensibility information associated with the specific target image.

According to an embodiment, the visualization information may be represented by attribute information about a particle effect. For example, the visualization information may express the scent reminiscent of the specific target image in the form of at least one of a shape, a size, a color, a lifetime, a direction, a moving speed, and a rotation speed of particles. Thus, the visualization information may provide information such as creation, flow, and extinction of a fluid.

According to another embodiment, the visualization information may be represented by at least one icon mapped to the specific target image. According to another embodiment, the visualization information may be represented by metaphorical objects that are mapped to a specific object.

For example, the metaphorical objects may include illustrations, photographs, constellations, or the like.

For example, the visualization information may be mixed with various attribute expressions, or may be represented by attribute information preconfigured by the user.

Thereafter, the processor 5700 may extract first associative visualization information when a plurality of visualization information is provided. The first associative visualization information may be visualization information having the highest similarity among the plurality of visualization information.

According to an embodiment, the processor 5700 may extract the first associative visualization information by using a softmax algorithm.

Thereafter, the processor 5700 may generate a first learning model (S1300). More specifically, the processor 5700 may generate the first learning model to which the first associative visualization information on the target image is reflected through machine learning. For example, the machine learning may use at least one algorithm among a supervised learning, a support vector machines (SVM), a random forest (RF), a Naïve Bayes (NB), an artificial neural network (ANN), a decision tree (C4.5), a Bayesian, and the like. Thereafter, the generated first learning model may be transmitted to the third storage unit 5150 by the communication unit 5700 and stored therein.

The processor 5700 may learn second basic data (S1500). In other words, the processor 5700 may extract second associative visualization information associated with specific sensing information.

More specifically, the processor 5700 may learn visualization information reminiscent of the second basic data. Here, the visualization information may be information that visually expresses olfactory sensibility information associated with the specific sensing information.

As described above, the visualization information may be expressed in the form of at least one of attribution information about the particle effects, icon information, and metaphorical objects, or may be expressed in the form preconfigured by the user.

Thereafter, the processor 5700 may extract second associative visualization information when a plurality of visualization information is provided. The second associative visualization information may be visualization information having the highest similarity among the plurality of visualization information. According to an embodiment, the processor 5700 may extract the second associative visualization information by using the softmax algorithm.

Thereafter, the processor 5700 may generate a second learning model (S1700). More specifically, the processor 5700 may generate the second learning model to which the second associative visualization information on the target image is reflected through machine learning. Thereafter, the generated second learning model may be transmitted to the third storage unit 5150 and stored therein.

In the scent visualization method according to an embodiment of the present disclosure, the above-described steps S1100 and S1300 and the above-described steps S1500 and S1700 are not limited to be performed in parallel. That is, the steps may be performed sequentially according to a configuration of the user.

Referring again to FIG. 5, the processor 5700 may obtain an associative image by applying the generated learning models (S3000). Here, the associative image may be an image combining the target image received from the display apparatus 1000 and the selected association effect. The step of generating the associative image using the learning model will be described in more detail with reference to FIG. 7.

Figure 7:
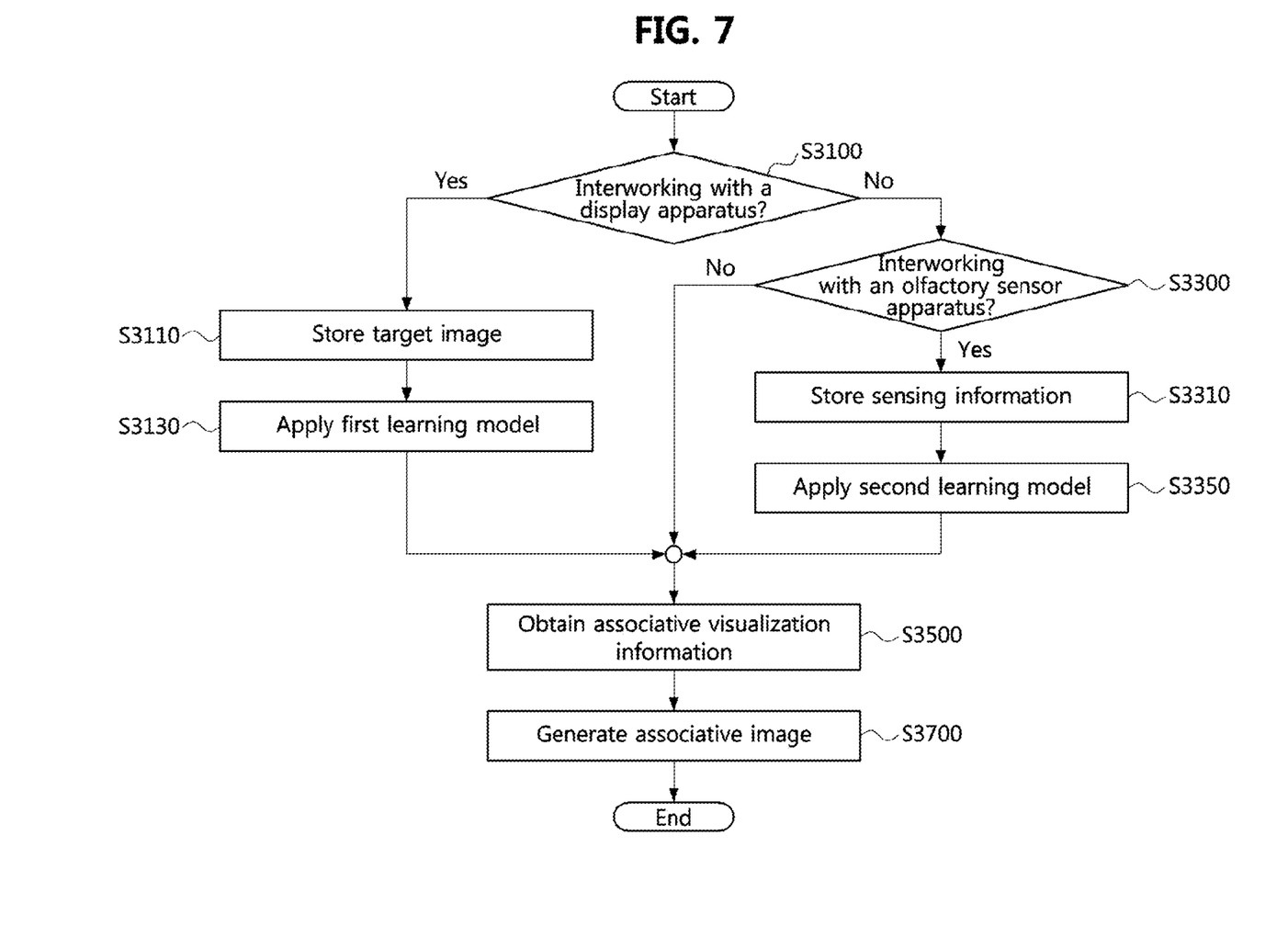
FIG. 7 is a flowchart illustrating a step of generating an associative image in a scent visualization method according to an embodiment of the present disclosure.

FIG. 7 is a flowchart illustrating a step of generating an associative image in a scent visualization method according to an embodiment of the present disclosure.

Referring to FIG. 7, the processor 5700 may determine an interworking state with at least one apparatus.

When the scent visualization apparatus 5000 is interworking with the display apparatus 1000 according to an embodiment (S3100), the processor 5700 may receive and store at least one target image (S3110). Thereafter, the processor 5700 may apply the received target image to the first generated learning model (S3310). Accordingly, the processor 5700 may output the first associative visualization information for the target image.

When the scent visualization apparatus 5000 is interworking with the olfactory sensor apparatus 3000 according to another embodiment (S3300), the processor 5700 may receive and store at least one sensing information (S3310). Thereafter, the processor 5700 may apply the received sensing information to the second generated learning model (S3350). Accordingly, the processor 5700 may output the second associative visualization information for the sensing information.

The processor 5700 may compare the generated first associative visualization information and the second associative visualization information. Accordingly, the processor 5700 may select associative visualization information having a higher similarity among the first and second associative visualization information (S3500).

Thereafter, the processor 5700 may generate an associative image by combining the target image received from the display apparatus 1000 and the selected associative visualization information (S3700).

Referring again to FIG. 5, the processor 5700 may transmit the generated associative image to the display apparatus 1000 (S5000). Accordingly, the user may remind a unique scent of the target image through the associative image displayed on the display apparatus 1000 without a separate scent diffusion apparatus.

As described above, the scent visualization system and method according to the embodiments of the present disclosure have been described. The scent visualization system and method may include a display apparatus, an olfactory sensor apparatus, and a scent visualization apparatus, may generate associative visualization information reminiscent of a scent from a target image and sensing information received from the apparatuses, and may provide an associative image combining the target image and the associative visualization information to the user, thereby providing low-cost, high-efficiency, and high-convenience scent visualization system and method.

The embodiments of the present disclosure may be implemented as program instructions executable by a variety of computers and recorded on a computer readable medium. The computer readable medium may include a program instruction, a data file, a data structure, or a combination thereof. The program instructions recorded on the computer readable medium may be designed and configured specifically for the present disclosure or can be publicly known and available to those who are skilled in the field of computer software.

Examples of the computer readable medium may include a hardware device such as ROM, RAM, and flash memory, which are specifically configured to store and execute the program instructions. Examples of the program instructions include machine codes made by, for example, a compiler, as well as high-level language codes executable by a computer, using an interpreter. The above exemplary hardware device can be configured to operate as at least one software module in order to perform the embodiments of the present disclosure, and vice versa.

A further embodiment comprises a processing means, for example a computer, or a programmable logic device, configured to or adapted to perform one of the methods described herein. A further embodiment comprises a computer having installed thereon the computer program for performing one of the methods described herein. In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are advantageously performed by any hardware apparatus.

While the embodiments of the present disclosure and their advantages have been described in detail, it should be understood that various changes, substitutions and alterations may be made herein without departing from the scope of the present disclosure.

What is claimed is:

1. A scent visualization method of a scent visualization apparatus interworking with a display apparatus and an olfactory sensor, the scent visualization method comprising:
   receiving a target image including a target object from the display apparatus;
   applying the target image to a first learning model;
   generating first associative visualization information about the target image from the first learning model;
   receiving sensing information from the olfactory sensor;
   applying the sending information to a second learning model;
   generating second associative visualization information on the sensing information from the second learning model;
   comparing the first associative visualization information and the second associative visualization information to select a target associative visualization information having a higher similarity, the target associative visualization information being one selected between the first associative visualization information and the second associative visualization information; and
   combining the selected target associative visualization information and the target image to generate an associative image.

2. The scent visualization method according to claim 1, wherein the first learning model is generated through machine learning by extracting visualization information representing first basic data which is olfactory sensibility information of the target object with visual attribute information, and extracting the first associative visualization information having a high similarity among the visualization information.

3. The scent visualization method according to claim 2, wherein the second learning model is generated through machine learning by extracting visualization information representing second basic data which is olfactory sensibility information of the sensing information with visual attribute information, and extracting the second associative visualization information having a high similarity among the visualization information.

4. The scent visualization method according to claim 3, wherein the visualization information is represented by at least one of an attribute representing a particle effect, an icon, an illustration, a photograph, and a constellation.

5. The scent visualization method according to claim 3, wherein the first associative visualization information and the second associative visualization information are extracted using a softmax algorithm.

6. The scent visualization method according to claim 1, wherein the display apparatus is a head mounted display (HMD) apparatus.

7. The scent visualization method according to claim 1, further comprising generating a least one scent corresponding to the sensing information by interworking with a scent diffusion apparatus.

8. A scent visualization apparatus comprising a processor and a memory storing at least one instruction executable by the processor, wherein when executed by the processor, the at least one instruction is configured to:
   interwork with a display apparatus and an olfactory sensor;
   receive a target image including a target object from the display apparatus;
   receive sensing information from the olfactory sensor;
   output first associative visualization information about the target image using a first learning model to which the target image is applied;
   output second associative visualization information about the sensing information using a second learning model to which the sensing information is applied;
   compare the first associative visualization information and the second associative visualization information to select a target associative visualization information having a higher similarity, the target associative visualization information being one selected between the first associative visualization information and the second associative visualization information; and
   combine the selected target associative visualization information and the target image to generate an associative image.

9. The scent visualization apparatus according to claim 8, further comprising a communication unit providing a communication network for interworking with the display apparatus and the olfactory sensor.

10. The scent visualization apparatus according to claim 8, further comprising a storage unit for storing data, wherein the storage unit comprises:
    a first storage unit storing first basis data which is olfactory sensibility information of the target image;
    a second storage unit storing second basic data which is olfactory sensibility information of the sensing information; and
    a third storage unit storing the first learning model and the second learning model.

11. The scent visualization apparatus according to claim 8, wherein the at least one instruction is further configured to:
    learn the first basic data;
    learn the second basic data;
    generate the first learning model; and
    generate the second learning model.

12. The scent visualization apparatus according to claim 8, wherein the first learning model is generated through machine learning by extracting visualization information representing the first basic data with visual attribute information, and extracting the first associative visualization information having a high similarity among the visualization information.

13. The scent visualization apparatus according to claim 12, wherein the second learning model is generated through machine learning by extracting visualization information representing the second basic data with visual attribute information, and extracting the second associative visualization information having a high similarity among the visualization information.

14. The scent visualization apparatus according to claim 13, wherein the visualization information is represented by at least one of an attribute representing a particle effect, an icon, an illustration, a photograph, and a constellation.

15. The scent visualization apparatus according to claim 13, wherein the first associative visualization information and the second associative visualization information are extracted using a softmax algorithm.

16. The scent visualization apparatus according to claim 8, wherein the display apparatus is a head mounted display (HMD) apparatus.

17. The scent visualization apparatus according to claim 8, wherein the at least one instruction is further configured to generate a least one scent corresponding to the sensing information by interworking with a scent diffusion apparatus.

18. A scent visualization system comprising:
a display apparatus for generating a target image including a target object;
an olfactory sensor for detecting a scent; and
a scent visualization apparatus for generating a target associative visualization information that reminds the scent from the target image received from the display apparatus and sensing information received from the olfactory sensor, and generating an associative image by combining the target associative visualization information and the target image,
wherein first associative visualization information about the target image is output using a first learning model to which the target image is applied, second associative visualization information about the sensing information is output using a second learning model to which the sensing information is applied, and associative visualization information having a higher similarity between the first associative visualization information and the second associative visualization information is selected as the target associative visualization information.

19. The scent visualization system according to claim 18, further comprising a scent diffusion apparatus generating at least one scent corresponding to the sensing information.

* * * * *